United States Patent [19]
Mabie

[11] 3,973,970
[45] Aug. 10, 1976

[54] ADDITIVE COMPOSITION FOR MAKING DENTAL MATERIALS

[75] Inventor: Curtis P. Mabie, Thurmont, Md.

[73] Assignee: The United States of America as represented by the Secretary of the Department of Health, Education and Welfare, Washington, D.C.

[22] Filed: Jan. 7, 1975

[21] Appl. No.: 539,236

[52] U.S. Cl. .................................. 106/35; 106/45; 106/58
[51] Int. Cl.² ...................... C09K 3/00; C04B 33/00
[58] Field of Search .......................... 106/35, 45, 58

[56] References Cited
UNITED STATES PATENTS

| | | | |
|---|---|---|---|
| 2,897,595 | 8/1959 | Lee | 106/46 |
| 3,704,146 | 11/1972 | Dulat | 106/45 |
| 3,880,662 | 4/1975 | Daskalon | 106/35 |

OTHER PUBLICATIONS

Chem. Abst., 62:282g.

*Primary Examiner*—Theodore Morris
*Attorney, Agent, or Firm*—Browdy and Neimark

[57] ABSTRACT

Addition of ammonium stabilized colloidal silica, borax and boric acid to the distilled water in which dental porcelain is fired greatly increases the firing range by reducing "balling" or edge rounding, and flow deformation. Greatly increased machinability and indefinitely prolonged green-biscuit strength is also obtained by the use the present additive without deleterious effects on the porcelain.

6 Claims, 5 Drawing Figures

ADDITIVE COMPOSITION FOR MAKING DENTAL MATERIALS

FIELD OF THE INVENTION

The present invention relates to a substitute for distilled water normally used in the fabrication or preparation of dental materials and more particularly, to an additive for use with dental porcelain for increasing the green-strength and firing range of the porcelain while greatly reducing the "balling" or edge rounding of the porcelain.

BACKGROUND OF THE INVENTION

Porcelain dental materials such as jacket crowns, inlays, veneer on metal and denture teeth are generally prepared by adding distilled water to raw porcelain and then conducting the two operations of condensation and densification. Condensation is herein defined as the process of green-biscuit preparation. Densification is defined as those pyro-bonding processes that form the mature porcelain.

Condensation is acheived by pressing or packing the porcelain material into the desired shape. Densification is accomplished by firing the condensed porcelain to an appropriate temperature. Depending upon the strength of the green-biscuit the shape may be manipulated either before or after firing by such techniques as machining.

Shrinkage and distortion of the material (green-biscuit) often occur upon firing. Additives have been tried in the wetting stage to develop green strength. However, no additives have been formulated specifically to prevent deformation in firing, particularly that known as "balling" wherein sharp edges become rounded off during firing. It is noteworthy that other properties of both the green-biscuit and the fired or final product which are necessary in order to have an acceptable dental product are adversely affected by all known additives.

For example, organic silicates, particularly tetraethyl silicate and sodium metasilicate have been recommended for use with dental porcelain in British Pat. No. 499,959. However, it has been found that the use of organic silicates for dental porcelain is undesirable because in the amounts required to restrict "balling", the green-body bulk density is too low. This poor initial packing causes excessive firing shrinkage. Also, in vacuum or reducing or inert atmospheric fires, char will be left behind. Furthermore, sodium metasilicate cannot be used because it does not satisfactorily restrict "balling" and causes severe and excessive opacification.

SUMMARY OF THE INVENTION

It is accordingly an object of the present invention to provide an additive for dental porcelains which avoids these drawbacks of the prior art.

It is another object of the present invention to provide an additive for use with dental porcelain which will not cause excessive firing shrinkage, not leave char behind and will not contribute to opacification.

It is yet another object of the present invention to provide an additive for use with dental porcelain which will inhibit rounding at the edges, or "balling", in the firing of the dental portion and, in general, restrict flow deformation.

It is still another object of the present invention to provide an additive for use with dental porcelain which will greatly increase green-body biscuit strength and machinability.

It is still another object of the present invention to provide an additive for use with dental porcelain which will indefinitely prolong green-body stength upon drying without renewed liquid additions, thus greatly improving the ease of handling in the dental laboratory.

It is yet another object of the present invention to provide an additive for use with dental porcelain which will greatly increase the firing range by inhibiting flow deformation and edge rounding, and also by suppressing the undesirable high gloss effect resulting from overfiring.

It is still another object of the present invention to provide an additive for use with dental porcelain which will significantly increase the attainable fired strength.

It is another object of the present invention to provide a dental porcelain green biscuit with increased and prolonged strength.

It is yet another object of the present invention to provide a dental porcelain having the above mentioned properties.

It is still another object of the present invention to provide a method of making a dental porcelain having the above mentioned properties.

These and other objects are achieved with additive solutions of a particular composition and character and comprising the use of from 1 to 8% ammonium stabilized colloidal silica in a distilled water solution containing 0.5 to 1.25% boric acid plus borax with weight ratios of boric acid to borax of 0.1 to 1.5. The additive solutions are added directly to the dental porcelain as substitute for distilled water. Upon becoming hard after air drying they may be machined. They may be vibrated and manipulated the same as prior art water prepared porcelains. The porcelain using the additive of the present invention may be used in the fabrication or preparation of all known dental porcelain material products such as jacket crowns, inlays, veneers on metal, or denture teeth. The invention may entail the use of either low or high firing porcelains. The present invention in general reduces process variables and thus increases ease of porcelain prosthetic device fabrication. The high green-body strength and machinability of raw porcelain prepared in accordance with the present invention may be expected to increase the ease of handling during the processing.

BRIEF DESCRIPTION OF THE DRAWINGS

FIG. 2 shows a comparison of two porcelain bars after firing.

FIG. 3 shows a comparison of two porcelain bars after firing at elevated temperature.

DETAILED DESCRIPTION OF PREFERRED EMBODIMENTS

The additive composition of the present invention essentially comprises an active ingredient composed of ammonium stabilized colloidal silica and a suitable flux which is water soluble and compatible with the colloid. Ammonium stabilized colloidal silica is knwon and is available commercially, for example, from DuPont Chemical Company under the tradename Ludox AS.

Particles of Ludox AS are discrete uniform spheres of silica which have no internal surface area or detectable crystallinity. They are dispersed in ammonium hydroxide which reacts with the silica surface to produce a negative charge. Because of the negative charge, the particles repel one another resulting in a stable product.

Figure 1:
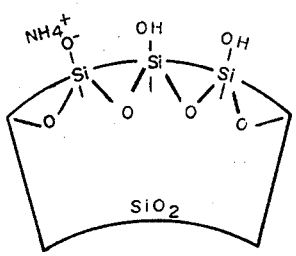
FIG. 1 shows the chemical designation of the surface configuration of ammonium stabilized colloidal silica.

Ludox AS is a 30% solution of silica solids. The particle size is 13–14 nm, and the specific surface area is 210–230 sq.m/g. The pH at 25°C is 9.6 and titratable alkali is 0.25% $NH_3$ and 0.09% $Na_2O$. The ratio of $SiO_2/NH_3$ (by weight) is 120, and the viscosity is 20 cp at 25°C. The weight per gallon at 25°C is 10.1 lb., a specific gravity at 25°C is 1.21, and the conductance at 20°C is 2630. The surface configuration may be seen in FIG. 1. Ludox AS may also be procured in 40% solution.

While Ludox AS is generally known for use as a binder used with refractory grains and fibers in high temperature mortars and cements, and in slip casting slurries, its properties for use with dental porcelain as in the present invention is highly unexpected and unobvious There are many standards which dental porcelain must meet in order for it to be acceptable in dental practice. That any additive could so improve the properties of dental porcelain, as the present invention, without detracting from any of the other necessary porperties is totally surprising and unexpected.

Any flux which will aid in maturation and development of bond strength may be used in the present invention as long as it is water soluble and compatible with the colloid. Examples include boric acid, borax, sodium phosphate and ammonium phosphate. The additive solution should contain approximately 0.5 to 1.25% flux. The preferred flux for use with the present invention is boric acid plus borax with weight ratios of boric acid to borax of 0.1 to 1.5.

Any known and acceptable dental porcelain may be used with the present invention. However, air fired low fusing Apco manufactured by Columbus Dental Manufacturing Company was used in the following examples. Apco Dentine Porcelain has the following approximate chemical composition: $SiO_2$ 63.45%, $AlO_3$ 18.04%, CaO 0.6%, $R_2O$ 7.87%, $B_2O_3$ 5.42% with an unknown quantity of SnO. Mineralogically it has been shown that this porcelain contains predominantly glass particles (80–32 $\mu m$) with subordinate amount of feldspar (32–16 $\mu m$).

Two sample preparations of the present invention will now be discussed. A flux solution was prepared by dissolving 0.5 gram each of borax and boric acid in 100 cc of distilled water. To make product preparation A, 4 parts by volume of flux solution were added to 1 part by volume of 30% ammonium stabilized $SiO_2$ (Ludox AS). To make product preparation B, 7.4 parts by volume of the flux solution were added to 2.6 parts by volume of the 30% ammonium stabilized colloidal silica (Ludox AS).

The dental products may then be made in the conventional manner as is currently done by those of ordinary skill in the art of making dental porcelain products by merely substituting the additive solution for the distilled water normally used to make a paste with the porcelain. A small portion of solution is mixed with raw porcelain powder until a paste of the proper consistency is made and the excess liquid is mopped up. The paste is then built up on the specimen and packed with again any excess liquid being removed. Precise compositions are not critical when making porcelain dental products.

To test the properties of additives A and B, test samples were made in appropriate shaped molds, for example cylindrical-, bar-, dumb-bell- or diamond-shaped molds. A small amount of the appropriate solution, whether distilled water or product A or B is added to the mold and weighed amounts of porcelain were poured and stirred and allowed to settle. Excess solution was withdrawn with absorbent paper and packed with 222 kg applied loads. The raw porcelain charge varied according to the size mold but normally was within about 0.25 to 2.00 grams. The testing included pull-tensile tests, diametrical-tensile tests, modulus of rupture tests, compressive green-strength tests, warpage tests, edge rounding or "balling" tests, fire shrinkage determinations, solubility determinations, density determinations and thermal expansion measurements.

Figure 2A:
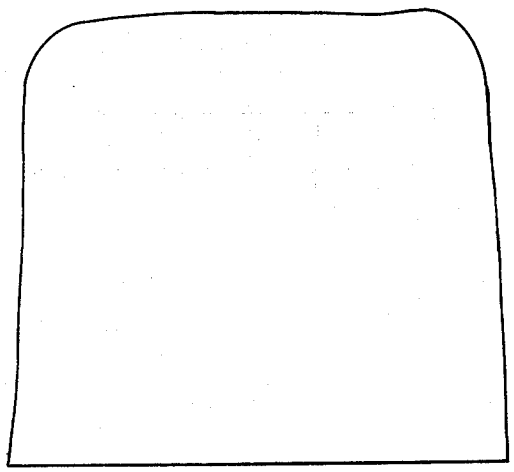
FIG. 2a is the end of a porcelain bar using a preparation of the present invention and FIG. 2b is the end of a porcelain bar nearly identically fired using the prior art distilled water preparation, at the same magnification.
Figure 2B:
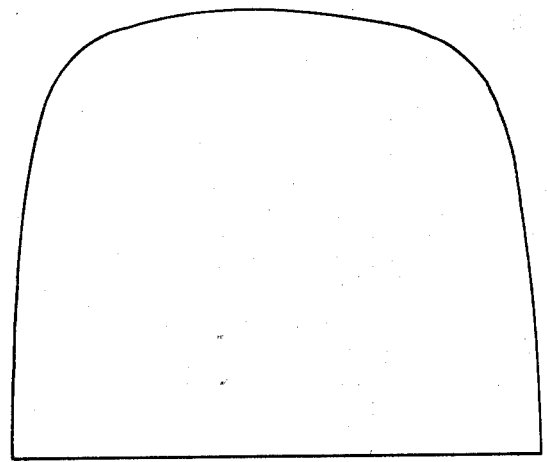
Figure 3A:
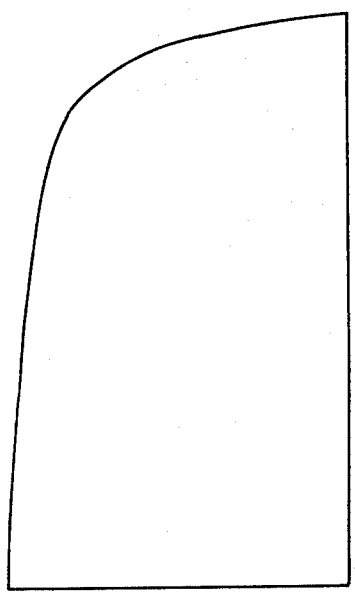
FIG. 3a is the end of a porcelain bar using one preparation of the present invention and FIG. 3b is the end of a porcelain bar using another preparation of the present invention and fired at an even more elevated temperature than FIG. 3a, at the same magnification.
Figure 3B:
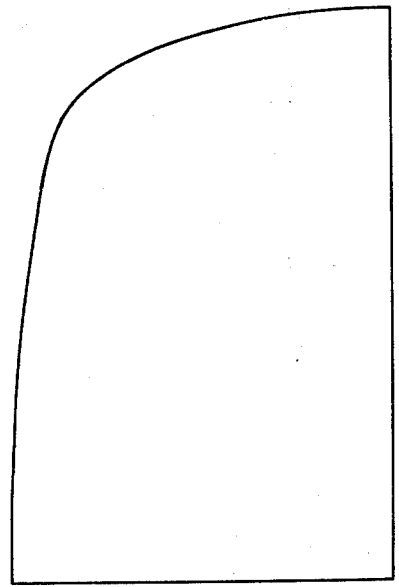

The edge rounding or "balling" restrictive effect obtained with the additive of the present invention compared to normal water preparations fired to essentially the same temperature is evident from FIGS. 2 and 3. FIG. 2 shows the rounding inhibition on the end of a porcelain bar using additive A preparation (1039° C, 25°C/min. heating rate for FIG. 1 a) compared to nearly identically and slightly less severely fired normal distilled water preparation (1038° C, 26°C/min. heating rate for FIG. 1 b).

FIG. 3 shows the restricted deformation at elevated temperature obtained with additive A (1065° C, 23°C/min. heating rate for FIG. 3 a) and additive B (1080° C, 24°C/min for FIG. 3 b).

Preparation A additive liquid can be seen to provide outstanding edge rounding restrictive effect when compared with normal water preparations, and preparation B additions resulted in even more restrictive effects. The preparation B liquid inhibits edge rounding to a greater extent than preparation A liquid does even when fired to 15°C higher (FIG. 3). From the study of edge rounding effects, at rates greater than 23°C/min., preparation A increases the peak firing range of the Apco porcelain used at least 20°C, and preparation B increases it by at least 35°C.

The compressive green-strength of Apco porcelain cylindrical pellets is greatly increased by the use of the additives of the present invention. Suitable short heat treatment on a hot plate at approximately 200°C, or a drying oven, is sufficient to create unfired preparation A liquid prepared biscuits with at least double the strength of the water prepared ones. For example, the greatest green-strength obtained by using water and pelletizing with 563 kg/cm² applied pressure is 7.6 kg/cm². The heat treatment of a preparation A additive pellet on a hot plate for 9 minutes, and with a total time after pelletizing of 15 minutes, can yield a body with a green-strength of 13.6 kg/cm².

With prolonged standing of more than 2 hours the unheated solution A prepared body can yield compressive strength as high as 20.2 kg/cm². The strength induced by additive use is retained indefinitely as can be seen from Table I hereinbelow. However, after 4 hours, the strength of the usual water preparations decreases to about half of that of the original. For example, when pelletizing with 563 kg/cm², compressive strength can deteriorate to 2.7–4.0 kg/cm² from the 6.1 to 7.6 kg/cm² obtainable immediately after forming.

As discussed hereinabove, in modern porcelains the loss in green-strength is very severe and the addition of ammonium stabilized silica sol in accordance with the present invention is of great advantage to them. When the green dental porcelain biscuit prepared with this silica sol is subjected to a brief heat treatment, compressive green strength may be doubled. A stable indefinitely strong machinable body is created. Normal

TABLE I

Compressive Green Strength Versus Time

| Specimen No. | Time, Air Drying, Hrs. | Compressive Strength, kg/cm²[1] | | Cylindrical Pellet Preparation Pressure, kg/cm²[2] |
|---|---|---|---|---|
| | | H₂O Added | Prep. No. 40 Added | |
| 1. | 0.15 | 6.1 | | 563 |
| 2. | 0.15 | 8.1 | | 704 |
| 3. | | | 5.3 | 563 |
| 4. | 0.23 | | 6.9 | " |
| 5. | 0.23 | | 5.8 | " |
| 6. | 0.42 | 7.0 | | " |
| 7. | 0.53 | | 5.8 | " |
| 8. | 1.17 | 7.6 | | " |
| 9. | 1.5 | | 9.7 | " |
| 10. | 2.0 | 7.3 | | " |
| 11. | 2.3 | | 20.2 | " |
| 12. | 3.6 | 3.5 | | " |
| 13. | 4.0 | 2.7 | | " |
| 14. | 4.6 | 3.5 | | " |
| 15. | 4.7 | | 17.7 | " |
| 16. | 5.0 | 3.6 | | " |
| 17. | 5.0 | | 19.4 | " |
| 18. | 6.0 | 4.0 | | " |
| 19. | 6.2 | 3.1 | | " |
| 20. | 7.7 | | 21.6 | " |
| 21. | 9.2 | | 18.8 | " |
| 22. | 9.4 | 3.8 | | " |
| 23. | 9.6 | 3.8 | | " |
| 24. | 63.3 | 2.8 | | " |
| 25. | 63.3 | | 20.0 | " |
| 26. | 200°C Hot plate Heating, 9 min.; Total time, 15 min. | | 13.6 | " |

[1]Rate of Load Application was 0.05"/min.
[2]Av. diameter was 0.64 cm., and length 1.33 cm.

To obtain immediately the greatly improved green-strength as for example when working or machining of the green biscuit is desired, it is merely necessary to allow the green biscuit to sit for a sufficient time to achieve the desired increase in strength. The time may be accelerated by heating up to a temperature of about 200°C.

The totality of the testing showed that there was no evidence that porcelain preparations using the additives of the present invention pack less easily than the water preparations. Furthermore, no drying shrinkage was noticed in either preparations prepared with water or with the additive of the present invention. The difference in the firing shrinkage and fired pellet density of similarly fired products using the present invention and using water is negligible and is of no practical importance.

All of the strength data accumulated, pull-tensile, diametrical-tensile and modulus of rupture, indicate that porcelains prepared with the product of the present invention are not weaker than equivalently fired water prepared porcelain. The preperation A porcelains may be fired to equivalent degrees of deformation as the water preparations with a significant increase in diameterical-tensile strength and modulus of rupture. Preparation B may be fired to strengths that are no less than those of equivalently deformed water preparations.

water prepared porcelain on drying out severely weakens.

The inhibition of "balling" and porcelain flow by additive use greatly increases the range over which the porcelain of the present invention may be fired. No apparent loss in translucency is encountered but gloss is slightly reduced by its use. This gloss reduction is probably an advantage because overfiring may induce too much gloss. Addition of a normal final glaze eliminates any gloss reduction effects. Also no reduction in microhardness, "Rockwell"Hardness, solubility or deleterious low temperature thermal expansion effects have been encountered. Additive use will also restrict "balling" in high-fusing porcelains.

It must be understood that the present invention is not limited to the particular porcelains disclosed herein but is applicable to any porcelain suitable for dental products. Similarly the method of making the porcelain is not critical as long as the preparation of the present invention is substituted for the distilled water previously used for mixing with raw porcelain powder mixture.

Various other silica and/or alumina gels may be used as the active ingredient of the additives of the present invention such as Ludox 130M which is an acidic aqueous dispersion of positively charged colloidal particles consisting of a dense silica core coated with positively charged polymeric alumina with a chemical composition of about 26% $SiO_2$ and 4% $Al_2O_3$. This product is defined in U.S. Pat. No. 3,007,878 which is hereby incorporated by reference. Also usable is chloride stabilized alumina product such as that sold under the same 5025 Cawoods Special Alumina Bond by Hammill and Gillespie Inc. and is disclosed in British Pat. No. 1,188,241. This material is a colorless low viscosity liquid with a pH of 2–3, a specific gravity of 1.3 and containing about 22% alumina and 10.3% soluble chloride. While these other silica and/or alumina products may cause an improvement of one or more properties, such as green strength and anti-balling properties, they are not as effective as ammonium stabilized silica in order to give an improvement in all of the significant properties discussed hereinabove without detriment to the other properties which are necessary in dental porcelain products.

It will be obvious to those skilled in the art that various changes may be made without departing from the scope of the invention and the invention is not to be considered limited to what is shown in the drawings and described in the specification.

What is claimed is:

1. In the method of making dental porcelain products, comprising making a paste of a liquid product and raw porcelain powder, compressing and firing to a temperature sufficient to bond the mixture into a mature porcelain, the improvement wherein said liquid product comprises a composition comprising an aqueous solution of a colloidal silica and/or alumina sol and a water soluble flux which is compatible with the colloid used.

2. A method in accordance with claim 1, wherein said colloidal silica and/or aluminum sol is ammonium stabilized silica sol.

3. A method in accordance with claim 2, wherein said flux is a combination of boric acid and borax.

4. A method in accordance with claim 3, wherein said composition comprises 1 to 8% ammonium stabilized colloidal silica and 0.5 to 1.5% flux, wherein said flux comprises boric acid and borax with a weight ratio of boric acid to borax of 0.1–1.5 : 1.

5. The dental porcelain product made in accordance with the method of claim 4.

6. A green biscuit for firing into a porcelain dental product comprising a compressed paste of raw dental porcelain powder and a composition comprising 1 to 8% ammonium stabliized colloidal silica and 0.5 to 1.5% flux, wherein said flux comprises boric acid and borax with a weight ratio of boric acid to borax of 0.1–1.5 : 1.

* * * * *